(12) United States Patent
Myla

(10) Patent No.: US 9,968,434 B2
(45) Date of Patent: May 15, 2018

(54) METHODS AND DEVICES FOR EMBOLIC PROTECTION

(71) Applicant: Subbarao V. Myla, Newport Coast, CA (US)

(72) Inventor: Subbarao V. Myla, Newport Coast, CA (US)

( * ) Notice: Subject to any disclaimer, the term of this patent is extended or adjusted under 35 U.S.C. 154(b) by 230 days.

(21) Appl. No.: 14/301,153

(22) Filed: Jun. 10, 2014

(65) Prior Publication Data
US 2014/0364897 A1 Dec. 11, 2014

Related U.S. Application Data

(60) Provisional application No. 61/833,223, filed on Jun. 10, 2013.

(51) Int. Cl.
*A61F 2/01* (2006.01)
*A61F 2/90* (2013.01)

(52) U.S. Cl.
CPC .............. *A61F 2/013* (2013.01); *A61F 2/90* (2013.01); *A61F 2002/011* (2013.01); *A61F 2002/016* (2013.01); *A61F 2230/0006* (2013.01); *A61F 2230/0069* (2013.01)

(58) Field of Classification Search
CPC ...... A61F 2/013; A61F 2/90; A61F 2002/011; A61F 2002/016
See application file for complete search history.

(56) References Cited

U.S. PATENT DOCUMENTS

| 4,494,531 | A * | 1/1985 | Gianturco | A61F 2/01 606/200 |
|---|---|---|---|---|
| 6,066,149 | A * | 5/2000 | Samson | A61B 17/221 606/127 |
| 6,325,815 | B1 * | 12/2001 | Kusleika | A61B 17/221 606/200 |
| 6,610,077 | B1 * | 8/2003 | Hancock | A61F 2/013 606/194 |
| 8,137,376 | B2 | 3/2012 | Clubb et al. | |
| 8,152,833 | B2 | 4/2012 | Zaver et al. | |
| 8,382,788 | B2 | 2/2013 | Galdonik et al. | |
| 2002/0045916 | A1 * | 4/2002 | Gray | A61F 2/01 606/200 |
| 2003/0040771 | A1 * | 2/2003 | Hyodoh | A61F 2/90 606/200 |

(Continued)

OTHER PUBLICATIONS

Emboline, Inc., "Emboline," www.emboline.com/technology.html, accessed Apr. 28, 2013, 2 pages.

(Continued)

*Primary Examiner* — Alexander Orkin
(74) *Attorney, Agent, or Firm* — Inskeep IP Group, Inc.

(57) ABSTRACT

An aortic flow diverter or filter is described that diverts particles away from the carotid vessels and right subclavian artery. The diverter includes a stent-like portion formed from a plurality of braided or woven wires that can radially self-expand. The stent-like portion is generally tubular and is fixed over the distal end of a catheter or shaft. A sheath is located over both the catheter and stent-like portion, maintaining the stent-like portion in a compressed configuration. When withdrawn proximally, the sheath releases the stent-like portion, allowing it to expand against the walls of the vessel.

9 Claims, 7 Drawing Sheets

(56) References Cited

U.S. PATENT DOCUMENTS

| | | | |
|---|---|---|---|
| 2003/0181942 A1* | 9/2003 | Sutton | A61B 17/0057 606/200 |
| 2007/0208373 A1* | 9/2007 | Zaver | A61F 2/01 606/200 |
| 2008/0255603 A1* | 10/2008 | Naor | A61F 2/00 606/200 |
| 2009/0326575 A1* | 12/2009 | Galdonik | A61F 2/01 606/200 |
| 2010/0152765 A1* | 6/2010 | Haley | A61F 2/01 606/200 |
| 2010/0185231 A1* | 7/2010 | Lashinski | A61F 2/01 606/200 |
| 2012/0065660 A1* | 3/2012 | Ferrera | A61F 2/01 606/198 |
| 2012/0310319 A1 | 12/2012 | Tieu et al. | |
| 2013/0131714 A1 | 5/2013 | Wang et al. | |
| 2013/0345739 A1* | 12/2013 | Brady | A61B 17/221 606/200 |
| 2014/0046358 A1* | 2/2014 | Cully | A61F 2/01 606/200 |

OTHER PUBLICATIONS

Scranton Gillette Communications, "CardioLogical Receives Patent for Aortic Embolic Protection Devices to Prevent During TAVR," *Diagnostic and Interventional Cardiology*, Apr. 12, 2013, www.dicardiology.com/article/cardiological-receives-patent-aortic-embolic-protection-devices-prevent-during-tavr, accessed Apr. 28, 2013, 2 pages.

Werner, Nikos, "Embolic Protection during TAVI Embrella," Universitätsklinikum Bonn, Bonn, Germany; presented at *Congenital and Structural Heart Interventions* (*CSI*), Frankfurt, Germany, Jun. 28-30, 2012, 14 pages.

Baumback, Andreas MD, FRCP, FESC, "Brain Damage—Will Embolic Protection Devices Reduce Strokes After TAVR?", Bristol Heart Institute, University Hospitals Bristol; presented at *Imaging in Cardiovascular Interventions* (*ICI*), Frankfurt, Germany, Jun. 27, 2012, 17 pages.

University Hospital, Essen, Germany, "Intraprocedural Intraaortic Embolic Protection With the EmbolX Device in Patients Undergoing Transaortic Transcatheter Aortic Valve Implantation (TAo-EmbolX)," ClinicalTrials.gov, clinicaltrials.gov/ct2/show/NCT01735513, updated Nov. 27, 2012, accessed Apr. 28, 2013, 3 pages.

TCTMD.com, "Embolic Protection Devices for TAVR Show Promise," *TCTMD, The source for Interventional Cardiovascular News and Education*, www.tctmd.com/show.aspx?id=110221&AspxAutoDetectCookieSupport=1, Nov. 10, 2011, accessed Apr. 28, 2013, 2 pages.

WIPO, U.S. International Search Authority, International Search Report and Written Opinion dated Oct. 29, 2014 in International Patent Application No. PCT/US2014/041777, 8 pages.

* cited by examiner

METHODS AND DEVICES FOR EMBOLIC PROTECTION

RELATED APPLICATIONS

This application claims priority to U.S. Provisional Application Ser. No. 61/833,223 filed Jun. 10, 2013 entitled Methods and Devices for Embolic Protection, which is hereby incorporated herein by reference in its entirety.

BACKGROUND

As the world population continues to age, cardiovascular procedures will grow in frequency and complexity. In order to improve the safety and efficacy of such procedures, the complication of embolism associated with those procedures must be addressed.

An embolism is when thrombus or atheroma or calcium breaks loose from a patient's vasculature during a procedure and migrates distally and lodges in a peripheral vessel causing ischemic injury to the end organ.

A particularly acute complication is a cerebral embolism where an emboli lodges in one of the arteries of the brain and thus causes an injury to the brain. Accordingly, in a preferred embodiment, the invention focuses primarily on cerebral protection during heart operations such as coronary artery bypass surgery (CABG) and valve replacement, the latter being performed either by open chest surgery or through percutaneous delivery, e.g., trans-catheter aortic valve replacement (TAVR).

Traditional cerebral protection during open or closed heart procedures has involved administration of blood thinners (e.g. anticoagulants). However, this approach is directed more to the risk that arises due to the bleeding caused by surgical incisions. Such blood thinners do not address complications where the embolism is not responsive to anticoagulation.

Other methods include the use of aortic cannulas which have filters incorporated (e.g., Embolex) in the aorta as a way of protecting the brain. However, the large size and rigidity of these cannulas make them somewhat cumbersome.

More recently, in connection with TAVR procedures, surgeons have used diverters or filtration devices such as CLARET and EMBRELLA. Information regarding these devices are described and explained in the following references:

1. "Embolic Protection during TAVI Embrella," Nikos Werner, Universitätsklinikum Bonn, Bonn, Germany, CS Frankfurt 2012.
2. "Brain Damage—Will Embolic Protection Devices Reduce Strokes After TAVR?", Andreas Baumback, MD, FRCP, FESC, Bristol Heart Institute, University Hospitals Bristol, ICI 2012.
3. "CardioLogical Receives Patent for Aortic Embolic Protection Devices to Prevent During TAVR," *Diagnostic and Interventional Cardiology*, Apr. 12, 2013, www.dicardiology.com/article/cardiological-receives-patent-aortic-embolic-protection-devices-prevent-during-tavr, accessed Apr. 28, 2013.
4. "Emboline," www.emboline.com/technology.html, accessed Apr. 28, 2013.
5. "Intraprocedural Intraaortic Embolic Protection With the EmboIX Device in Patients Undergoing Transaortic Transcatheter Aortic Valve Implantation (TAo-EmboIX)," ClinicalTrials.gov, clinicaltrials.gov/ct2/show/NCT01735513, accessed Apr. 28, 2013.
6. "Embolic Protection Devices for TAVR Show Promise," TCTMD, *The source for Interventional Cardiovascular News and Education*, www.tctmd.com/show.aspx?id=110221&AspxAutoDetectCookieSupport=1, accessed Apr. 28, 2013.

These devices can essentially be divided into two categories: 1. Flow diverters where the emboli are diverted from entering vessels, e.g., the cerebral vessels; and, 2. Filtration devices where the emboli are captured and removed from the blood stream entirely.

The reliability and effectiveness of these devices is yet to be reliably verified. The need for some type of embolism protection, however, remains essential. Accordingly, there is an ongoing need for the development of systems and methods of protecting patients from emboli that are safe and effective. Accordingly, it is an object of the present invention to provide a system and method of more effectively providing protection from embolism to a patient during surgical procedures, and particularly protection from cerebral embolism.

SUMMARY OF THE INVENTION

One embodiment of the present invention is directed to an aortic flow diverter or filter that diverts particles away from the carotid vessels and right subclavian artery. Preferably, the diverter includes a stent-like portion formed from a plurality of braided or woven wires that can radially self-expand. The stent-like portion is generally tubular and is fixed over the distal end of a catheter or shaft. A sheath is located over both the catheter and stent-like portion, maintaining the stent-like portion in a compressed configuration. When withdrawn proximally, the sheath releases the stent-like portion, allowing it to expand against the walls of the vessel.

In one embodiment, the filter is positioned through the right subclavian artery, over the opening of the right common carotid artery and into the left common carotid artery. The sheath is withdrawn, allowing the stent-like portion to expand. A trans-catheter aortic valve replacement (or other similar procedure) is performed to repair or replace an aortic valve. Once the valve procedure is complete, the sheath is advanced over the stent-like portion and the filter is removed from the patient.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
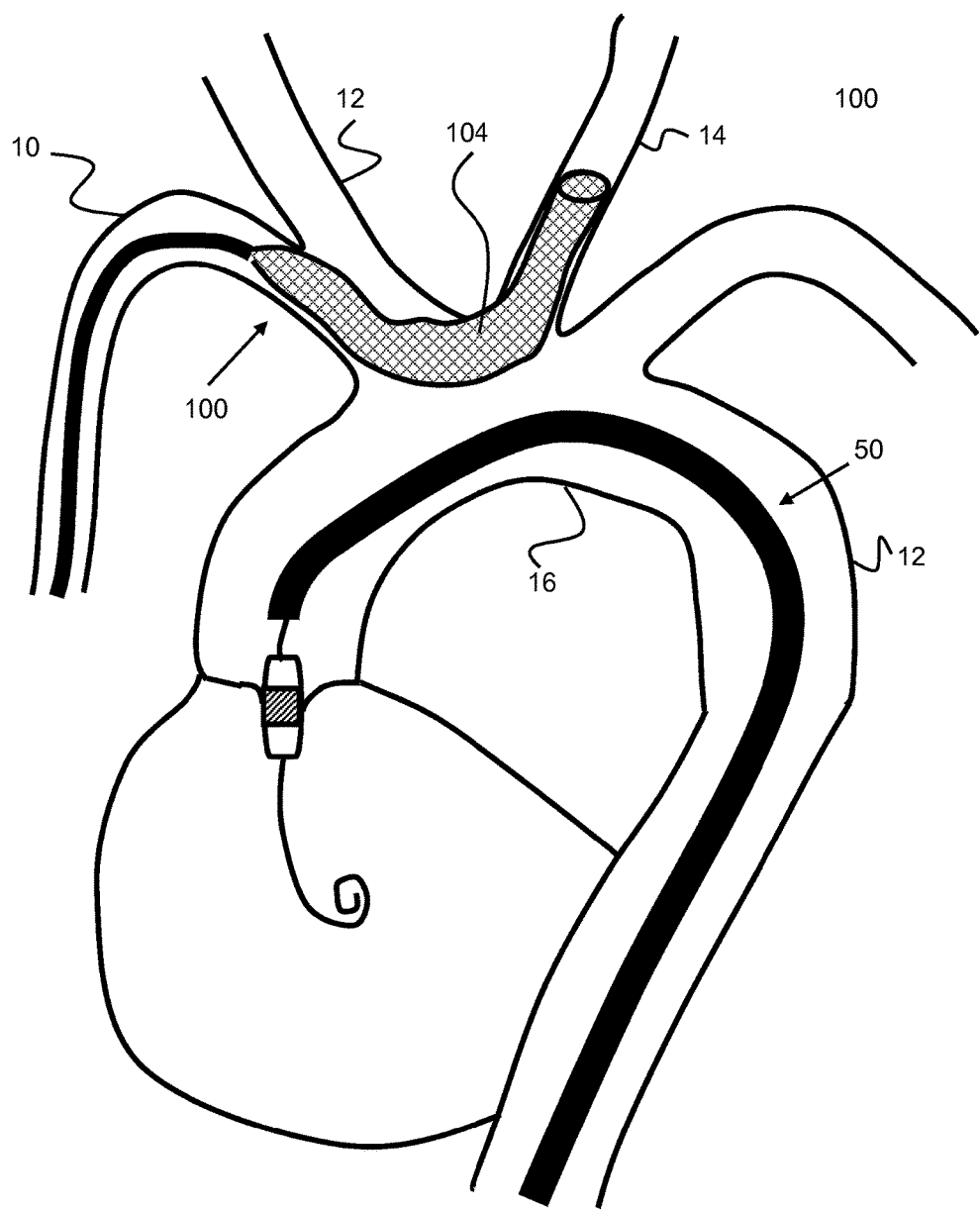
FIG. 1 is a rendering of one preferred embodiment of an aortic flow diverter (AFD) in accordance with the present invention shown being used during a TAVR procedure.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

In accordance with one embodiment of the present invention, a dual layer self-expanding Nitinol frame stent-like device is used as a flow diverter during cardiovascular procedures to prevent cerebral embolism.

Such a stent-like device used in the manner herein disclosed reduces the embolic load to the brain by effectively diverting the particles away from the carotid vessels and right subclavian artery. One reason that such effectiveness is obtained is because the device achieves superior wall apposition.

Moreover, using a stent-like device (or other similarly configured device) in this manner is low profile and thus avoids taking up space in the femoral artery (which must remain open for TAVR devices 50) and avoids the aortic arch 16. Hence, the device and technique substantially (if not completely) avoids impeding the valve replacement procedure.

Referring to FIG. 1, an aortic flow diverter 100 having a double layer Nitinol retrievable self-expanding stent-like portion 104 is shown in its deployed state extending from the right subclavian artery 10, over the opening of the right common carotid artery 12 and into the left common carotid artery 14. This deployment is shown in the context of a TAVR procedure TAVR catheter 50. However, the aortic flow diverter 100 can be used in any type of heart procedure including more traditional aortic valve replacement (AVR) procedures.

Due to the flexibility and expandability of the woven/braided stent-like portion 104 of the diverter 100, superior apposition of the diverter frame against the inner walls of the vessels is achieved. This ensures that a minimum number and minimum size of emboli are allowed into the cerebral arteries. Hence, the braiding and/or mesh characteristics of the woven/braided stent-like portion 104 of the diverter 100 divert such emboli away from the cerebral arteries.

In a preferred embodiment the woven/braided stent-like portion 104 of the diverter 100 is a tubular, dual-layer, self-expanding, Nitinol frame stent-like member made by Microvention, Inc. under the name CASPER. A representation of this stent can be found in U.S. Publication No. 2012/0310319 entitled Stent, published Dec. 6, 2012, which is herein incorporated by reference in its entirety.

Referring to FIGS. 2A-2F, one embodiment of a method for deploying and retrieving an aortic flow diverter 100 in accordance with the present invention is disclosed.

Figure 2A:
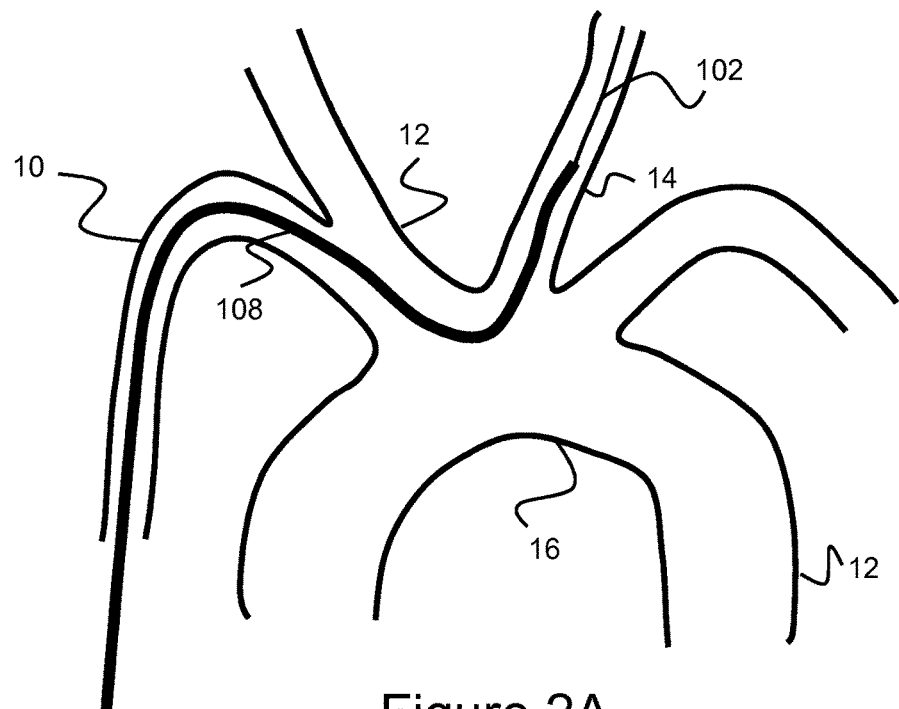
FIGS. 2A-2F are renderings of the various steps of deploying and retrieving an aortic flow diverter in accordance with one preferred embodiment of the present invention.

Referring to FIG. 2A, a guidewire 102 is directed from the RSCA 10 to the LCCA 14 of the patient. In a preferred embodiment the guidewire 102 is a stiff 0.035" Amplatz guidewire. A catheter 104 (e.g., a Simmons 2 catheter) is then delivered over the guidewire 102.

Figure 2B:
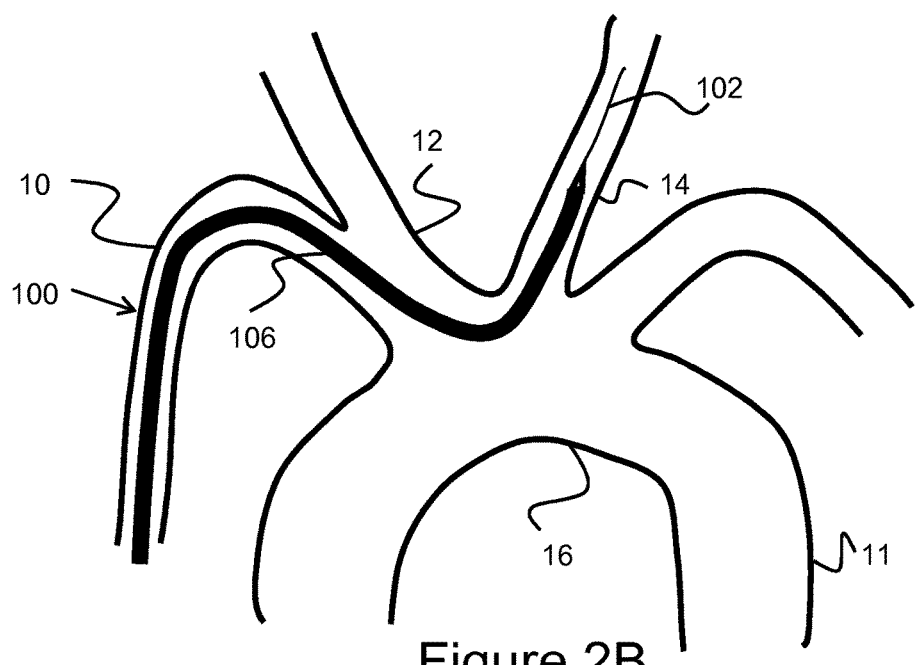

Referring to FIG. 2B, a sheath 106 (e.g. 6F in size) containing the aortic flow diverter 100 compressed on a catheter shaft 108 of a delivery catheter 108 (shown in FIGS. 3A and 3B) is then placed over the guidewire 102. The sheath 106 and catheter 108 are advanced over the guidewire, through the RSCA 10 to the LCCA 14 of the patient. In a preferred embodiment, the sheath 106 is a 6F Cook sheath or 6F Terumo Pinnacle sheath.

Figure 2C:
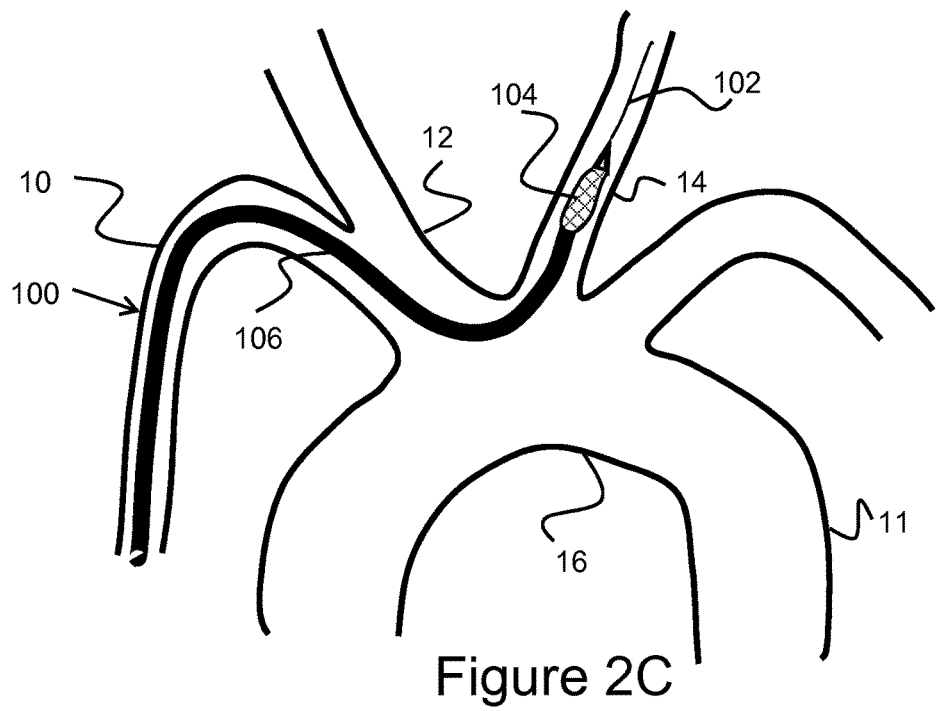

Referring to FIG. 2C, deployment of the aortic flow diverter 100 is initiated by withdrawing the sheath 106 to expose the tubular, stent-like portion 104 on the catheter shaft 120, after purging the system of any air bubbles.

Figure 2D:
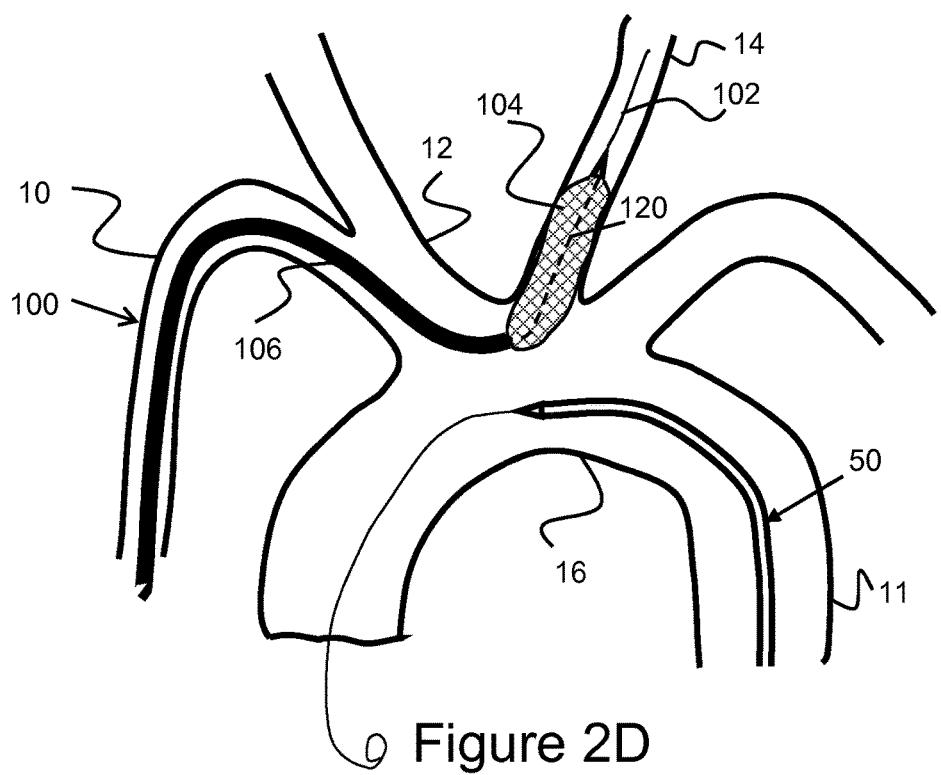

Referring to FIG. 2D, further deployment of the diverter 100 is shown as the sheath 106 continues to be retracted. As the stent-like portion 104 is exposed, it self-expands radially against the walls of the vessels. Also shown are the initial steps of a TAVR procedure where a TAVR catheter 50 is advanced through the femoral artery and into the aorta 11.

Figure 2E:
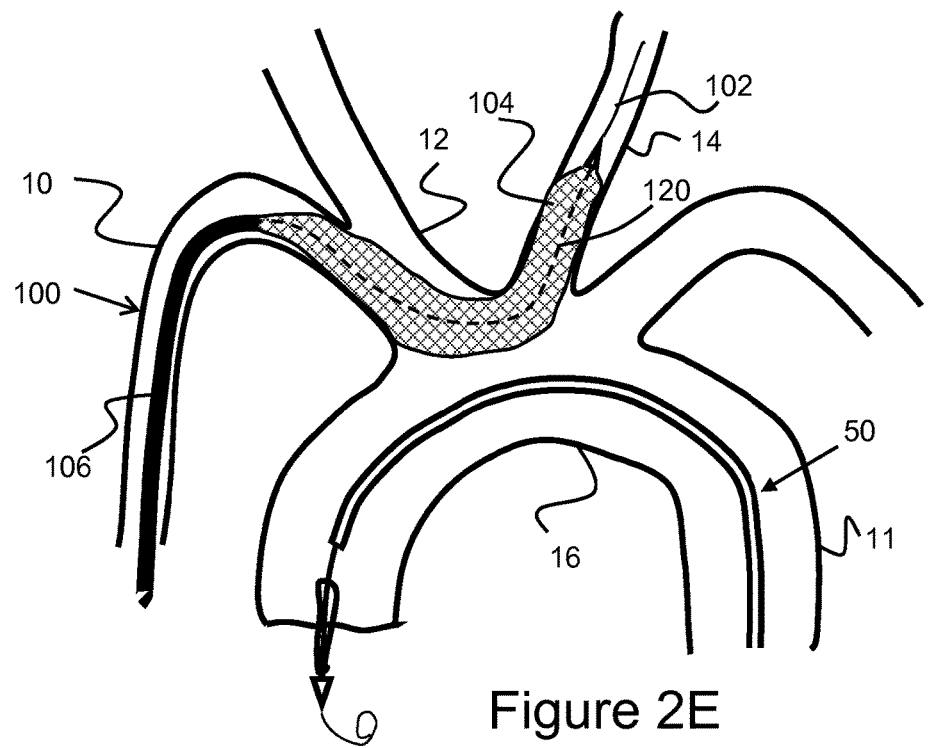

Referring to FIG. 2E, full deployment of the stent-like portion 104 of the diverter 100 is depicted, as the sheath 106 is retracted into the RSCA 10. Due to the wall apposition of the stent-like portion 104, any emboli resulting from the TAVR procedure are diverted away from the cerebral arteries.

Figure 2F:
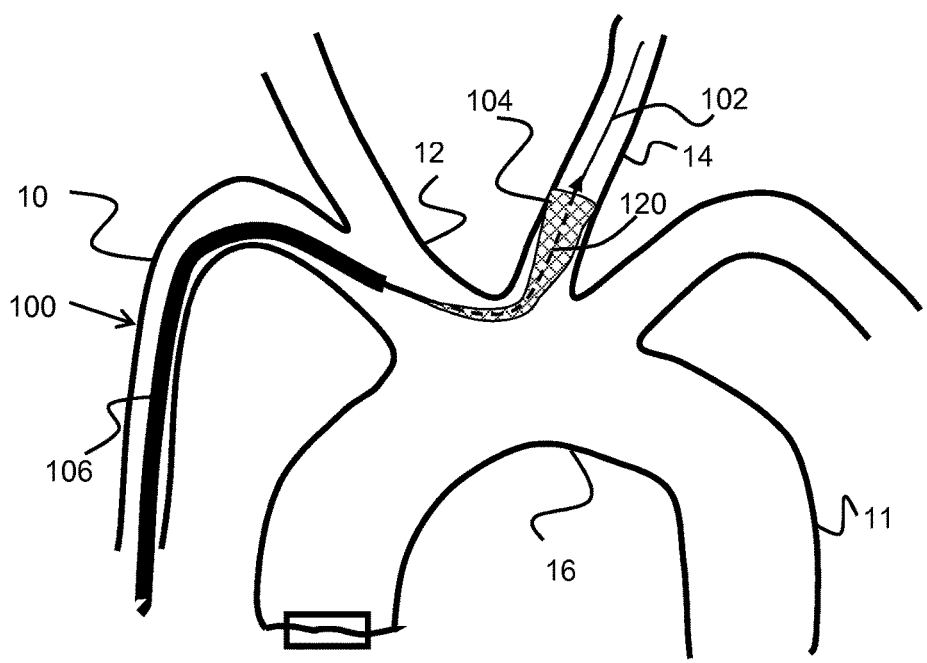

Referring to FIG. 2F, the diverter 100 is retrieved by advancing the sheath 106 in a distal direction and thereby causing the stent-like portion 104 to be contracted inwardly on to the catheter shaft 120. Once the stent-like portion 104 is fully captured in the sheath 106, the entire apparatus (i.e., the sheath 106, catheter 108, diverter 100, and guidewire 102) is removed from the patient.

Figure 3A:
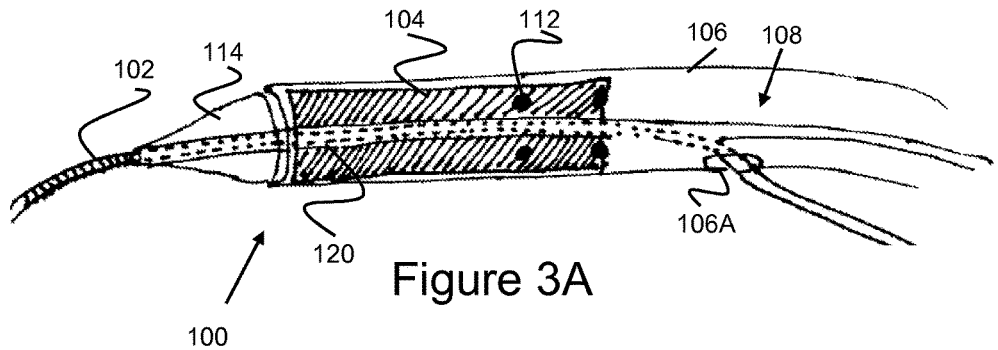
FIGS. 3A-3B are renderings of preferred embodiments of the working end of an aortic flow diverter in accordance with the present invention.

Referring to FIG. 3A, the distal working end of the diverter 100, catheter 108, and sheath 106 in the closed position is shown. As can be seen, the sheath fully captures the stent-like portion 104 of the diverter 100. A nose cone 114 at the distal end of the catheter shaft 120 allows smooth advancement of the device into the carotid vessels. In order to ensure proper placement of the diverter 100, radiopaque markers 112 are disposed on the proximal and/or distal ends of the stent portion of the stent-like portion 104. Additionally, the sheath 106 may include a monorail opening 106A near its distal end for over-the-wire use.

Figure 3B:
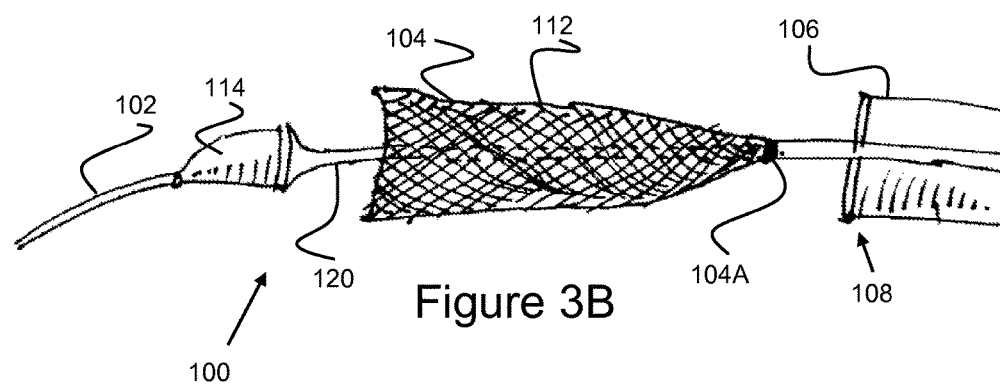

Referring to FIG. 3B, the working end of the diverter 100 in the open position is shown. As can be seen, the sheath 106 has been withdrawn proximally, thus allowing the stent-like portion 104 to expand. The nosecone 114 is separated from the distal end of the stent-like portion 104 of the diverter 100 by the radial expansion of the stent-like portion 104 peeling away from the shaft 120. The proximal portion of the stent-like portion 104, however, remains fused (e.g., by an adhesive, metal band, or welding) at point 104A on the shaft 120, preventing it from opening and allowing the stent-like portion 104 to be easily retrieved.

Preferably, the stent-like portion is woven or braided with at least two different diameter wires. For example, larger diameter wires 156 (e.g., 0.002-0.004 inches) can form a more rigid framework while smaller diameter wires 158 (e.g., 0.0010-0.0020 inches) can be woven to form a relatively small pour size (e.g. 150-200 microns). Preferably, both of these wires are made from Nitinol and are electropolished. These wires 156 and 158 can be woven into a single layer or the larger diameter wires 156 can be woven into an outer layer and the smaller diameter wires can be woven into an inner layer that is physically connected to the outer layer at various locations.

Figure 4:
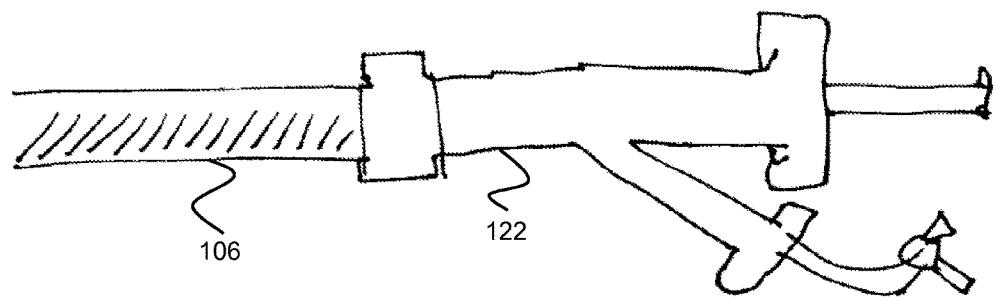
FIG. 4 is a rendering of a preferred embodiment of the back end of an aortic flow diverter in accordance with the present invention.

Referring to FIG. 4, the back end of the sheath 106 is connected with a traditional Touhey Borst adapter 122. The shaft 120 and stent-like portion 104 are movable in and out of the adapter 122 over the guide wire 102 into and out of the vessels as needed.

Figure 5:
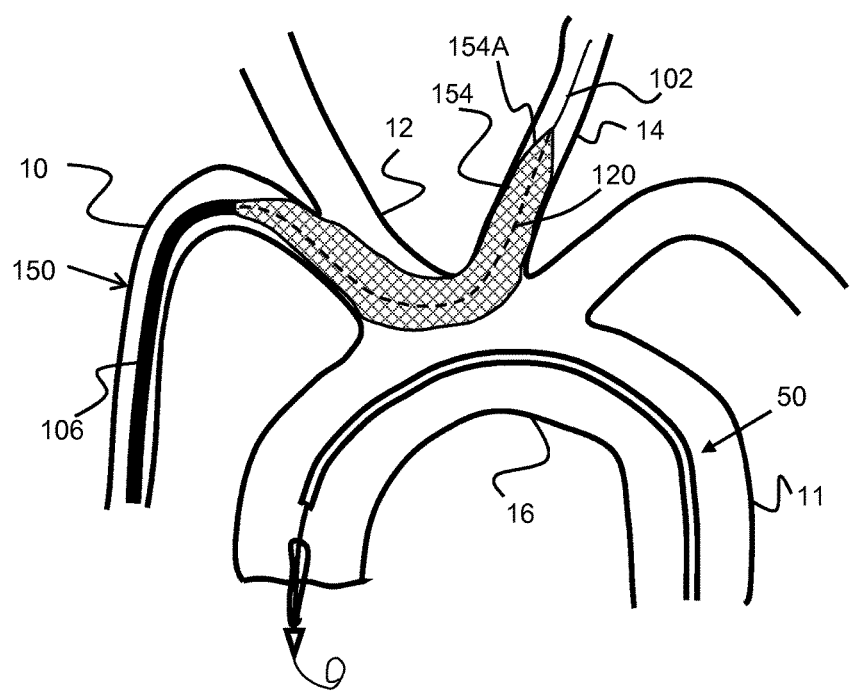
FIG. 5 is a rendering of a preferred embodiment of an aortic flow diverter in accordance with the present invention shown being used during a TAVR procedure; and, FIGS. 6A and 6B is a rendering of a preferred embodiment of an aortic flow diverter.
Figure 6A:
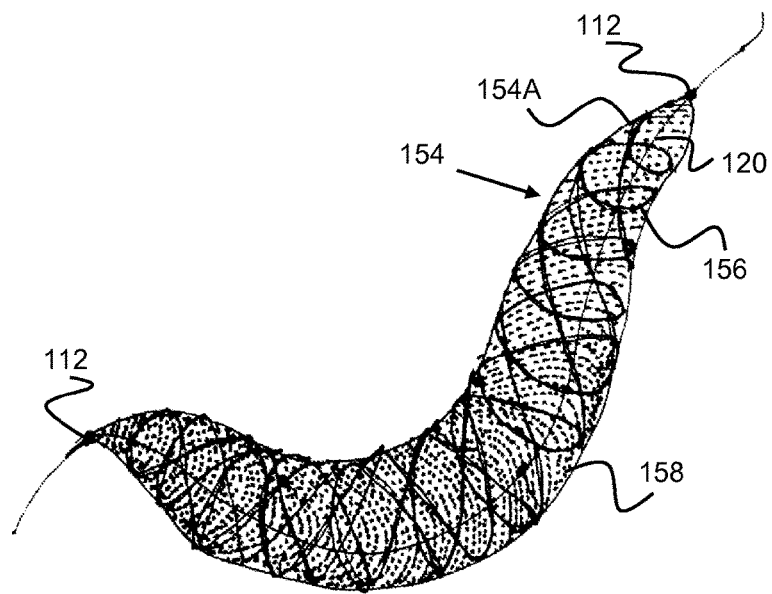
Figure 6B:
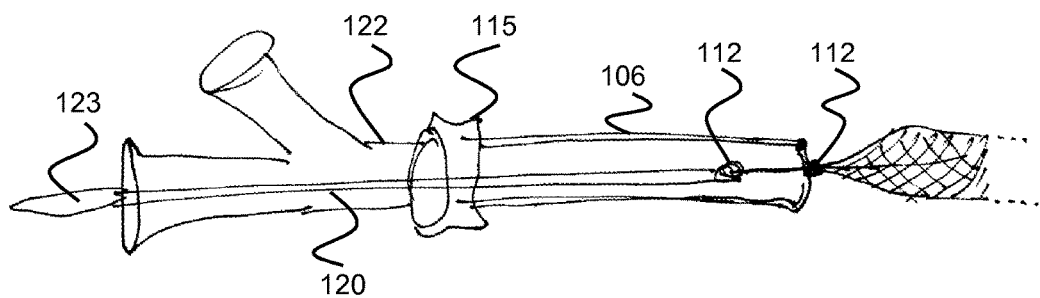

Referring to FIGS. 5, 6A, and 6B, another embodiment of a diverter 150 is shown wherein the stent-like portion 152 has a tapered and/or closed distal end 154A just below the nosecone with which it is fused to provide distal filtration. The proximal end is similar to that shown in FIG. 4, in which the sheath 106 is connected to a Touhey Borst via a hub 115. Additionally, the inner shaft 120 may include a handle 123.

In one embodiment, the pore size or cell size of the outer layer of the dual layer stent be 200-250 microns. This pore/cell size together with the radial expansion characteristics of inner frame/layer of the dual layer stent provides both the radial strength needed to give radial conformity and yet is still deliverable as well as maximize flow diversion. Small pore size reduces the particles that enter the stent and cerebral vessels during the filtration process.

In a preferred embodiment, e.g., see FIG. 5, the distal end of an outer layer of the dual layer stent is closed just beyond the inner layer. This configuration provides supplemental filtration of the left carotid artery and traps any material that enters the first layer of the dual layer stent. In another embodiment, the distal end of the outer layer remains open while the distal end of the inner layer is closed.

In another embodiment, the distal end of the stent-like portion can include a plurality of anchors to help maintain its position within the left common carotid artery. For example, such anchors could include a plurality of spikes, hooks, coils, or similar structures that are radially disposed on an outer surface of the stent-like portion.

In another embodiment, the stent-like portion has a length between 3-12 inches.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of protecting a patient from embolism during a surgical procedure comprising:
   directing a delivery catheter through the right subclavian artery of a patient to a left common carotid artery of the patient;
   deploying a stent-like device in said left common carotid artery and said right subclavian artery from said delivery catheter such that apposition of said stent-like device is substantially achieved on the walls of said left common carotid artery and said right subclavian artery; said stent-like device having an outer, tubular layer woven from wires having a diameter within a range of about 0.002 to 0.004 inch, and an inner, tubular layer woven from wires within a range of about 0.0010 to 0.0020 inch; said outer, tubular layer being disposed over said inner, tubular layer and being physically connected to said inner layer at a plurality of locations; said inner tubular layer and said outer tubular layer both having substantially the same length within a range of 3-12 inches; said inner tubular layer being open at its distal end and a distal end of said outer tubular layer being closed to form a cone shape distally beyond said inner layer;
   performing a valve replacement procedure;
   retrieving said stent-like device.

2. The method of claim 1, wherein said deploying said stent-like device further comprises proximally retracting a sheath and allowing radial expansion of said stent-like device.

3. The method of claim 1, wherein a proximal end of said stent-like device is fixed to a shaft positioned through said stent-like device.

4. The method of claim 3, wherein a distal end of said stent-like device is fixed to a shaft positioned through said stent-like device.

5. The method of claim 1, wherein said deploying said stent-like device is followed by diverting passage of emboli into said right subclavian artery and said left common carotid artery with said stent-like device.

6. The method of claim 1, wherein said deploying said stent-like device is followed by capturing emboli from blood passing into said right subclavian artery and said left common carotid artery with said stent-like device.

7. The method of claim 1, further comprising a plurality of anchor members radially disposed on said outer tubular layer.

8. The method of claim 1, wherein said inner tubular layer forms a pore size between 150 to 200 microns, and said outer tubular layer forms a pore size between 200 to 250 microns.

9. A method of protecting a patient from embolism during a surgical procedure comprising:
   advancing a delivery catheter system through the right subclavian artery of a patient to a left common carotid artery of the patient;
   proximally retracting a tubular sheath to expose a stent-like device located on a distal end of an inner catheter shaft, so as to allow said stent-like device to radially expand from a first compressed diameter to a second expanded diameter; said stent-like device having an outer, tubular layer woven from wires having a diameter within a range of about 0.002 to 0.004 inch, and an inner, tubular layer woven from wires within a range of about 0.0010 to 0.0020 inch; said outer, tubular layer being positioned over said inner, tubular layer and physically connected to said inner layer at a plurality of locations; said inner tubular layer and said outer tubular layer both having substantially the same length within a range of 3-12 inches; said outer tubular layer being open at its distal end and a distal end of said inner tubular layer being closed to form a cone shape;
   continuing to proximally retract said tubular sheath until said stent-like device is exposed and in said second expanded diameter between said left common carotid artery and said right subclavian artery;
   performing an aortic valve replacement procedure;
   distally advancing said sheath over said stent-like device so as to contract said stent-like device from said second expanded diameter to said first compressed diameter.

* * * * *